(12) United States Patent
Suorsa et al.

(10) Patent No.: US 6,824,515 B2
(45) Date of Patent: *Nov. 30, 2004

(54) ULTRASOUND-GUIDED ABLATION CATHETER AND METHODS OF USE

(75) Inventors: Veijo T. Suorsa, Sunnyvale, CA (US); David K. Swanson, Mountain View, CA (US); Dorin Panescu, Sunnyvale, CA (US); Harm TenHoff, Mountain View, CA (US); James G. Whayne, Saratoga, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/305,256

(22) Filed: Nov. 25, 2002

(65) Prior Publication Data

US 2003/0153907 A1 Aug. 14, 2003

Related U.S. Application Data

(63) Continuation of application No. 09/750,439, filed on Dec. 28, 2000, now Pat. No. 6,508,765, which is a continuation of application No. 09/227,281, filed on Jan. 6, 1999, now Pat. No. 6,206,831.

(51) Int. Cl.$^7$ .......................... A61B 8/12; A61B 18/14
(52) U.S. Cl. ........................ 600/439; 600/467; 601/2; 606/41; 607/99
(58) Field of Search .................... 600/439, 467, 600/314; 606/41; 607/99, 113, 122; 601/2

(56) References Cited

U.S. PATENT DOCUMENTS

| | | |
|---|---|---|
| 4,706,681 A | 11/1987 | Breyer et al. |
| 4,917,097 A | 4/1990 | Proudian et al. |
| 4,998,933 A | 3/1991 | Eggers et al. |
| 5,178,620 A | 1/1993 | Eggers et al. |
| 5,228,442 A | 7/1993 | Imran |
| 5,295,484 A | 3/1994 | Marcus et al. |
| 5,385,148 A | 1/1995 | Lesh et al. |
| 5,409,000 A | 4/1995 | Imran |
| 5,419,767 A | 5/1995 | Eggers et al. |
| 5,456,259 A | 10/1995 | Barlow et al. |
| 5,487,391 A | 1/1996 | Panescu |
| 5,571,088 A | 11/1996 | Lennox et al. |
| 5,590,659 A | 1/1997 | Hamilton et al. |
| 5,598,848 A | 2/1997 | Swanson et al. |
| 5,606,975 A | 3/1997 | Liang et al. |
| 5,630,837 A | 5/1997 | Crowley |
| 5,640,371 A | 6/1997 | Schmidt et al. |

(List continued on next page.)

FOREIGN PATENT DOCUMENTS

| | | | |
|---|---|---|---|
| WO | WO 96/00036 | 1/1996 | ........... A61B/17/36 |
| WO | WO 98/29032 | 1/1998 | ........... A61B/5/05 |

OTHER PUBLICATIONS

J. E. Zimmer et al., *The Feasibility of Using Ultrasound for Cardiac Ablation*, IEEE Transactions on Biomedical Engineering, vol. 42, No. 9, Sep., 1995, pp. 891–897.

*Primary Examiner*—Lee S. Cohen
(74) *Attorney, Agent, or Firm*—Townsend and Townsend and Crew, LLP

(57) ABSTRACT

The present invention provides ultrasound-guided ablation catheters and methods for their use. In one embodiment, a tissue ablation apparatus (2) includes a flexible elongate body (12) having proximal (14) and distal (12) ends. A plurality of spaced-apart electrodes (24) are operably attached to the flexible body near the distal end. A plurality of transducer elements (28) are disposed between at least some of the electrodes. Transducers assist the physician in determining whether or not the ablation elements are in contact with the tissue to be ablated.

11 Claims, 7 Drawing Sheets

U.S. PATENT DOCUMENTS

| | | |
|---|---|---|
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,713,363 A | 2/1998 | Seward et al. |
| 5,735,280 A | 4/1998 | Sherman et al. |
| 5,749,833 A | 5/1998 | Hakki et al. |
| 5,752,518 A | 5/1998 | McGee et al. |
| 5,769,847 A | 6/1998 | Panescu et al. |
| 5,840,030 A | 11/1998 | Ferek-Petric et al. |
| 5,846,204 A | 12/1998 | Solomon |
| 5,954,649 A | 9/1999 | Chia et al. |
| 6,053,868 A | 4/2000 | Geistert et al. |
| 6,206,831 B1 * | 3/2001 | Suorsa et al. ............... 600/439 |
| 6,240,307 B1 | 5/2001 | Beatty et al. |
| 6,490,474 B1 | 12/2002 | Willis et al. |
| 6,508,765 B2 * | 1/2003 | Suorsa et al. ............... 600/439 |
| 6,516,807 B1 | 2/2003 | Panescu et al. |

* cited by examiner

ULTRASOUND-GUIDED ABLATION CATHETER AND METHODS OF USE

CROSS-REFERENCES TO RELATED APPLICATIONS

This application is a Continuation of U.S. Appl. Ser. No. 09/750,439, filed on Dec. 28, 2000, and issued on Jan. 21, 2003 as U.S. Pat. No. 6,508,765; which is a Continuation of U.S. Appl. Ser. No. 09/227,281, filed Jan. 6, 1999 and issued on Mar. 27, 2001 as U.S. Pat. No. 6,206,831, the complete disclosures of which are incorporated herein by reference for all purposes.

BACKGROUND OF THE INVENTION

The invention relates generally to the field of ablation catheters, and in particular, to ultrasound-guided ablation catheters.

Physicians make use of catheters today in medical procedures that are best performed by gaining access into interior regions of the body. For example, in electrophysiological therapy, ablation is used to treat cardiac rhythm disturbances. Such a therapy may be used, for instance, to treat atrial fibrillation by forming long, thin lesions of different curvilinear shapes in heart tissue.

During these procedures, a physician steers a catheter through a main vein or artery into the interior region of the heart that is to be treated. An ablation element carried on the distal end of the catheter is positioned near the tissue that is to be ablated. For such treatments, the delivery of ablating energy must be closely governed to avoid incidence of tissue damage and coagulum formation. Further, the ablation catheters must be precisely positioned adjacent to and preferably in contact with the tissue to be treated, to insure the lesions are properly located.

Physicians and staff performing diagnostic and therapeutic procedures, such as electrophysiological therapy, typically require an imaging system to assist them in positioning the ablation catheter. Mini-transesophageal echocardiography (mini-TEE) probes are available, however, these probes must be swallowed or inserted down the patient's throat. Such probes are poorly tolerated by patients unless they are fully anesthetized. Further, these probes can be rather large (i.e., 20 French in diameter), use complex transducer configurations and may have difficulty in detecting tissue contact by the ablation elements.

Hence, it is desirable to provide an effective apparatus which assists the physician in determining whether the ablation elements are in contact with the tissue to be ablated. It is further desirable to have such imaging systems small enough to enter narrow and tortuous regions of the patient's vasculature. It is further desirable to have such imaging systems be located coincidental with the ablation elements to ensure tissue contact prior to ablation.

SUMMARY OF THE INVENTION

The present invention provides ultrasound-guided ablation catheters and methods for their use. Catheters and systems of the present invention will be particularly useful for precise positioning of ablation catheters prior to ablation of cardiac tissue, such as that required for the treatment of atrial fibrillation. Systems of the present invention use ultrasound transducers in the distal end of an ablation catheter to assist the operator in determining whether or not the ablation elements are in contact with the tissue to be ablated.

In one embodiment, the present invention provides a tissue ablation apparatus comprising a flexible elongate body having a proximal end and a distal end. A plurality of spaced-apart electrodes are operably attached to the flexible body near the distal end. A plurality of transducer elements are disposed between at least some of the electrodes. In this manner, transducer elements are positioned to assist the physician in detecting whether or not tissue contact is made by the proximate electrodes.

In one aspect, each electrode has at least one transducer element adjacent thereto. Preferably, the electrodes and transducer elements are operably attached to the flexible body in an alternating fashion. Still more preferably, the number of transducer elements exceeds the number of electrodes by at least one. In this manner, each electrode would have a transducer element distal thereof and another transducer element proximal thereof. By determining that the transducer elements are in contact with the tissue, the physician can presume that the intervening electrode is similarly in contact with the tissue.

In one aspect, the ablation apparatus further includes a plurality of insulators operably attached to the flexible body. The insulators operate to insulate the transducer elements from the electrodes. In one particular aspect, the flexible body has an outer diameter that is less than about eight (8) French. Ablation apparatus having such a size are sufficiently small enough to pass through the tortuous regions of a patient's vascular system.

In one aspect of the present invention, the electrodes are spaced apart from adjacent electrodes by a gap, preferably, a gap that is between about 1.5 mm and about 3.0 mm. Preferably, at least one of the transducer elements is operably attached to the flexible body in each gap. In this manner, transducer elements and electrodes are operably attached to the body in an alternating fashion.

In one particular aspect, the transducer elements comprise cylindrical transducer elements. The cylindrical elements each have a throughhole, and the elements are positioned so that a longitudinal axis of the flexible body passes through the throughholes. In this manner, the transducer elements present a 360 degree outer surface to the surrounding tissue. Therefore, the transducer elements need not be rotated to produce an image within a 360° image plane. In another aspect, the electrodes comprise generally cylindrical electrodes having an inner surface and an outer surface. The electrodes are positioned so that the inner surfaces face the longitudinal axis of the flexible body.

In one particular aspect, the apparatus includes between about two and about fourteen electrodes, and between about three and about fifteen transducer elements. Preferably, the electrodes and transducer elements are adapted to be connected to a controller. An ablation apparatus further preferably comprises a temperature sensing element operably attached to the flexible body. Such temperature sensing elements may be used, for example, to help monitor tissue temperatures near the ablation elements.

The invention further provides an exemplary system for ablating tissue. The system comprises an ablation apparatus ostensibly as previously described. The system includes a controller in electrical communication with the ablation elements and the transducer elements. In one aspect, the ablation elements comprise a plurality of electrodes. Alternatively, the ablation elements comprise a plurality of ablation transducer elements. In this manner, ablation may occur through the use of RF ablation or through ultrasound ablation. An exemplary description of acoustic ablation using transducer elements is described in U.S. Pat. No. 5,630,837, the complete disclosure of which is hereby incorporated by reference. It will be appreciated by those skilled in the art that other ablation elements may be used within the scope of the present invention.

Preferably, the controller comprises an ultrasound imaging and ablation controller. In this manner, ultrasound imaging is used to detect tissue contact by the ablation apparatus. The ablation of desired tissue then can occur.

In one aspect, the system further includes a plurality of leads with at least one lead operably attached to each of the ablation elements and each of the transducer elements. The plurality of leads preferably are in electrical communication with the controller to permit electrical signals to be transmitted from the controller to the ablation and transducer elements. The leads also permit signals to be sent from the transducer elements to the controller.

In a particular aspect, the system further includes a multiplexer operably attached to the flexible body, preferably near the distal end, and in electrical communication with the controller. At least some of the leads are operably attached to the multiplexer. The multiplexer operates to determine which transducer element receives electrical signals from the controller. By using a multiplexer at the distal end, the number of wires connecting the controller to the distal end may be reduced. By reducing the number of wires passing through an interior lumen of the flexible body, the outer diameter of the flexible body likewise can be reduced. Such a multiplexer will be particularly beneficial for apparatus having a relatively large number of transducer elements which together would use more wires than the multiplexer.

In one particular aspect, the transducer elements comprise cylindrical transducer elements. In this manner, the transducer elements need not be rotated to produce images within an image plane.

The invention further provides a method of ablating tissue. The method includes providing a tissue ablation apparatus as previously described with the electrodes and transducer elements being in electrical communication with a controller. The ablation apparatus is inserted into a patient and positioned proximate a tissue to be ablated. The transducer elements are energized and a plurality of reflected signals are received from the transducer elements. The method includes processing the reflected signals with the controller to determine if the transducer elements are in contact with the tissue to be ablated. If the controller determines that at least one of the transducer elements is in contact with the tissue, at least one of the electrodes is activated to ablate the tissue.

In one aspect, an ablation apparatus is provided having transducer elements and electrodes operably attached to the body in an alternating fashion. In another aspect, the reflected signals are processed to determine if one of the transducer elements is in contact with the tissue. If one of the transducer elements is in contact with the tissue, an adjacent electrode is activated to ablate the tissue.

In one aspect of the method, the reflected signals are processed to determine if all of the transducer elements are in contact with the tissue. In still another aspect, the method further includes repositioning the ablation apparatus if the controller determines that at least one of the transducer elements is not in contact with the tissue. In still another aspect, the ablation apparatus further includes a multiplexer operably attached to the body and in electrical communication with the transducer elements. The multiplexer operates to coordinate the order in which the transducers are energized.

The invention further provides a method of ablating tissue including the step of providing a tissue ablation apparatus having an elongate body, a plurality of ablation elements and a plurality of transducer elements. The ablation and transducer elements are operably attached to the body in an alternating fashion. The method includes inserting the ablation apparatus into a patient and positioning the ablation apparatus within the patient so that the ablation apparatus is proximate a tissue to be ablated. The transducer elements are energized and a plurality of reflected signals are received from the transducer elements. The method includes processing the reflected signals to determine if the transducer elements are in contact with the tissue to be ablated and activating at least one of the ablation elements to ablate the tissue if the controller determines that at least one of the transducer elements is in contact with the tissue.

In one aspect, the transducer elements are activated to ablate tissue using ultrasound energy. In another aspect of the method, the ablation elements include a plurality of electrodes for supplying current to the tissue. Alternatively, the ablation elements comprise a plurality of ablation transducers that operate to ablate the tissue using ultrasound energy.

Other features and advantages of the invention will appear from the following description in which the preferred embodiment has been set forth in detail in conjunction with the accompanying drawings.

A DETAILED DESCRIPTION OF THE PREFERRED EMBODIMENT

Figure 1:
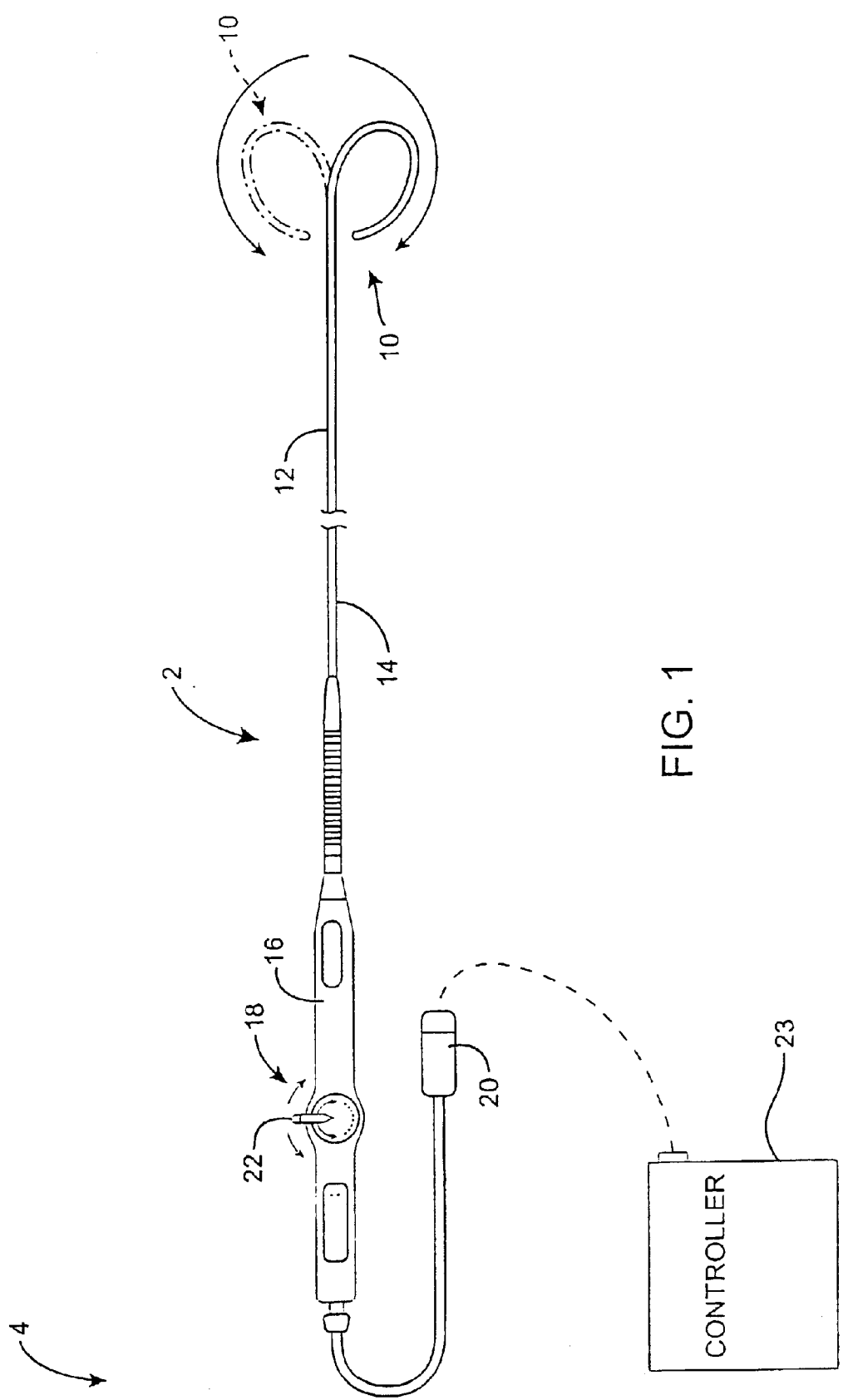
FIG. 1 depicts an overall view of a system for ablating tissue according to the present invention.

FIG. 1 depicts an exemplary tissue ablation apparatus 2 as part of a tissue ablation system 4 according to the present invention. Ablation apparatus 2 comprises a flexible elongate body 12 having a distal end 10 and a proximal end 14. Proximal end 14 includes a handle 16 containing a steering mechanism 18. Steering mechanism 18 includes a steering lever 22 which operates a cam wheel (not shown) to maneuver flexible distal end 10 as shown by the arrows in FIG. 1. System 4 includes a connector 20 which connects with a controller 23 for operation of ablation apparatus 2 as further described below. Controller 23 is capable of providing electrical input to ablation apparatus 2 as needed to image and ablate within a patient's body. It will be appreciated by those skilled in the art that steering mechanism 18 can vary from that shown in FIG. 1 within the scope of the present invention. Exemplary steering mechanisms are described in International Application No. PCT/US94/11748, the complete disclosure of which is hereby incorporated by reference for all purposes.

Tissue ablation apparatus 2 depicted in FIG. 1 will be particularly useful in the treatment of atrial fibrillation by positioning distal end 10 within a desired region of the heart. To enter the right atrium, the physician can direct elongate body 12 through a conventional vascular introducer through the femoral vein. For entry into the left atrium, the physician can direct elongate body 12 through a conventional vascular introducer retrograde through the aortic and mitral valves. For the treatment of atrial fibrillation, it is believed that formation of long thin legions of different curvilinear shapes is required. Catheters and ablation apparatus 2 of the present invention may be used to ablate heart tissue containing abnormal electrical pathways, such as arrhythmogenic foci. Further details of tissue ablation apparatus 2 are shown in FIGS. 2 and 3.

Figure 2:
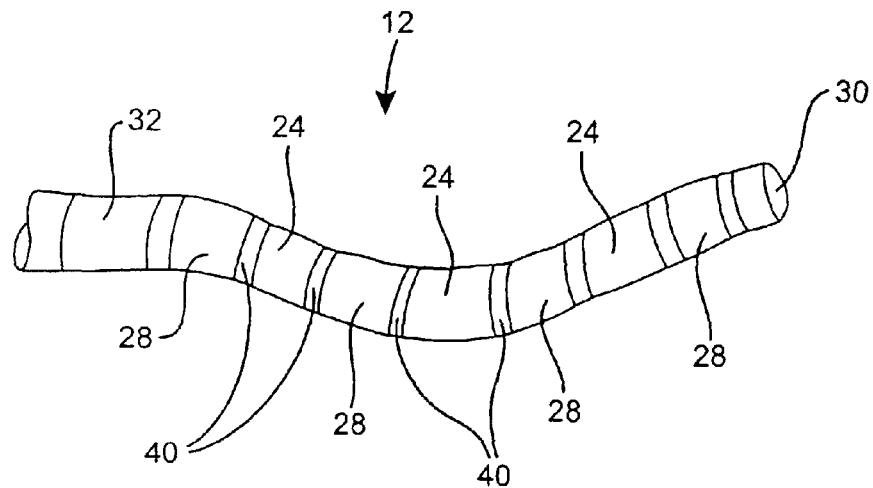
FIG. 2 depicts the distal end of a flexible elongate body as part of a tissue ablation system of the present invention.
Figure 3:
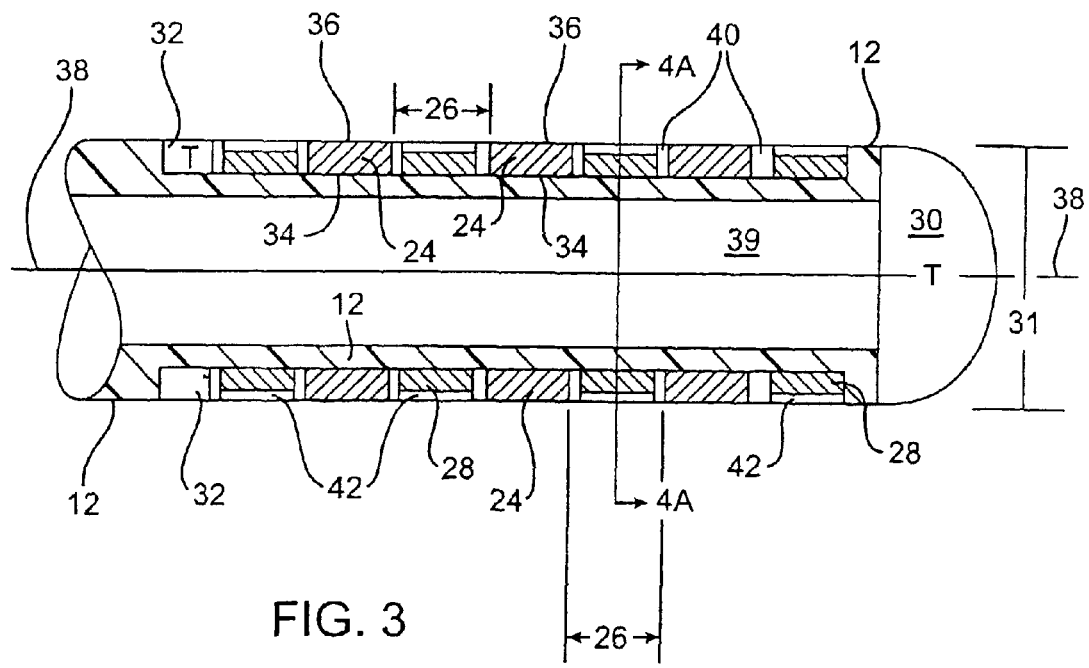
FIG. 3 depicts a cross-sectional side view of the flexible elongate body shown in FIG. 2.

FIGS. 2 and 3 depict elongate body 12 having a plurality of spaced-apart ablation elements 24, each separated by a gap 26 from adjacent ablation elements 24. Interspaced amongst ablation elements 24 are a plurality of transducer elements 28. Preferably, ablation elements 24 and transducer elements 28 are operably attached to body 12 in an alternating fashion. Ablation apparatus 2 preferably includes between about two and about fourteen ablation elements, and between about three and about fifteen transducer elements. More preferably, apparatus 2 has at least one more transducer element 28 than ablation elements 24. A temperature sensor 30 is provided at distal end 10 and a proximal temperature sensor 32 is provided proximal to ablation elements 24. Temperature sensors 30 and 32 preferably comprise thermocouples. Temperature sensors 30 and 32 also may comprise thermistors and the like within the scope of the present invention. Temperature sensors or thermocouples 30 and 32 operate to detect the temperature in the region of ablation. A plurality of insulators 40 are provided between transducer elements 28 and ablation elements 24. Insulators 40 may comprise polyimide, polyesters, teflon or the like to insulate transducer elements 28 from ablation elements 24.

Figure 4A:
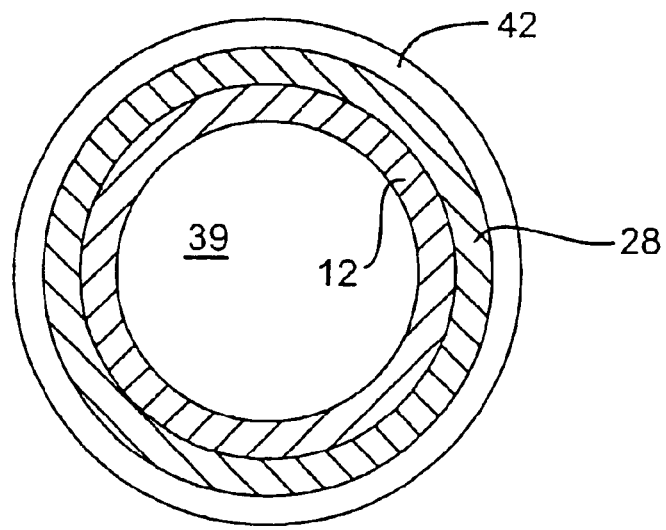
FIG. 4A depicts a cross-sectional end view of the flexible body shown in FIG. 3, taken along line 4A—4A.
Figure 4B:
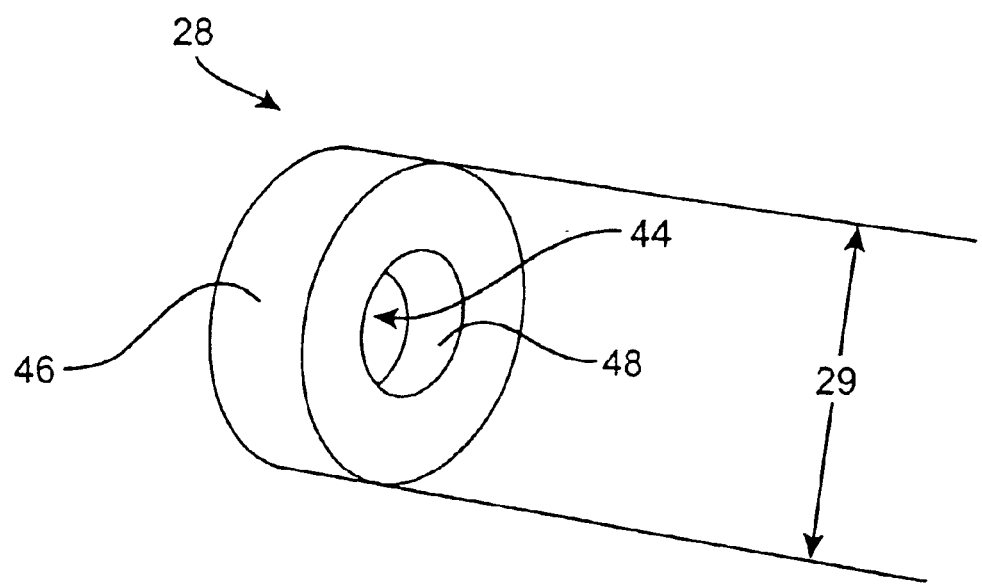
FIG. 4B depicts an overall view of a cylindrical transducer element as part of a tissue ablation apparatus according to the present invention.

Transducer elements 28 preferably comprise cylindrical transducer elements as best shown in FIGS. 4A–4B. Transducer elements 28 include an outer face 46 and an inner face 48. Inner faces 48 of transducer elements 28 are positioned such that a longitudinal axis 38 of body 12 passes through a throughhole 44 of each transducer element 28. In such a manner, transducer elements 28 are configured to expose outer faces 46 to surrounding tissue and fluid within the patient. In this manner, transducer elements 28 may operate to image within a 360° plane that is generally perpendicular to longitudinal axis 38 without the need to rotate body 12 or transducers 28. It will be appreciated by those skilled in the art that other transducer shapes may be used within the scope of the present invention. For example, transducer elements 28 may comprise rectangular or elliptical transducer elements operably attached to distal end 10. Transducer elements 28 may comprise piezocomposite materials, piezoceramics (such as PZT), piezoplastics, and the like.

As best shown in FIG. 3, transducers 28 each may include a matching layer 42, or multiple matching layers 42, operably attached to the outer face 46 of each transducer element 28. Matching layers 42 operate to improve transducer element 28 performance. In part due to the fact transducer elements 28 are used primarily as distance-to-tissue detectors, transducer elements 28 also can operate without matching layers 42 within the scope of the present invention.

Transducer elements 28 have an outer diameter 29. Outer diameter 29 can be less than an outer diameter 31 of flexible elongate body 12 or, alternatively, about equal to diameter 31. Preferably, diameter 31 of body 12 is less than about eight (8) French to permit the introduction of apparatus 2 into a patient's tortuous vasculature.

Gap 26 separates adjacent ablation elements 24. Gap 26 preferably is between about 1.5 mm and about 3.0 mm in width. Gap 26, however, can be larger or smaller in size and need not be of uniform size between each two adjacent ablation elements 24. Similarly, each gap 26 need not contain a transducer element 28, and gap 26 may contain more than one transducer element 28 within the scope of the present invention. However, preferably at least some gaps 26 contain transducer elements 28, and more preferably, each gap 26 between ablation elements 24 contains one transducer element 28.

Elongate body 12 preferably includes a working lumen 39 through which longitudinal axis 38 passes. As best shown in FIG. 4A, matching layer 42 extends around the outer surface of transducer element 28. Matching layer 42 is operably attached to transducer element 28, preferably using epoxy or the like. Transducer element 28 can be operably attached to elongate body 12 in a variety of manners, including by epoxy. The use of lumen 39 is best shown in FIGS. 5A and 5B which depict two alternative embodiments of tissue ablation apparatus 2 of the present invention.

Figure 5A:
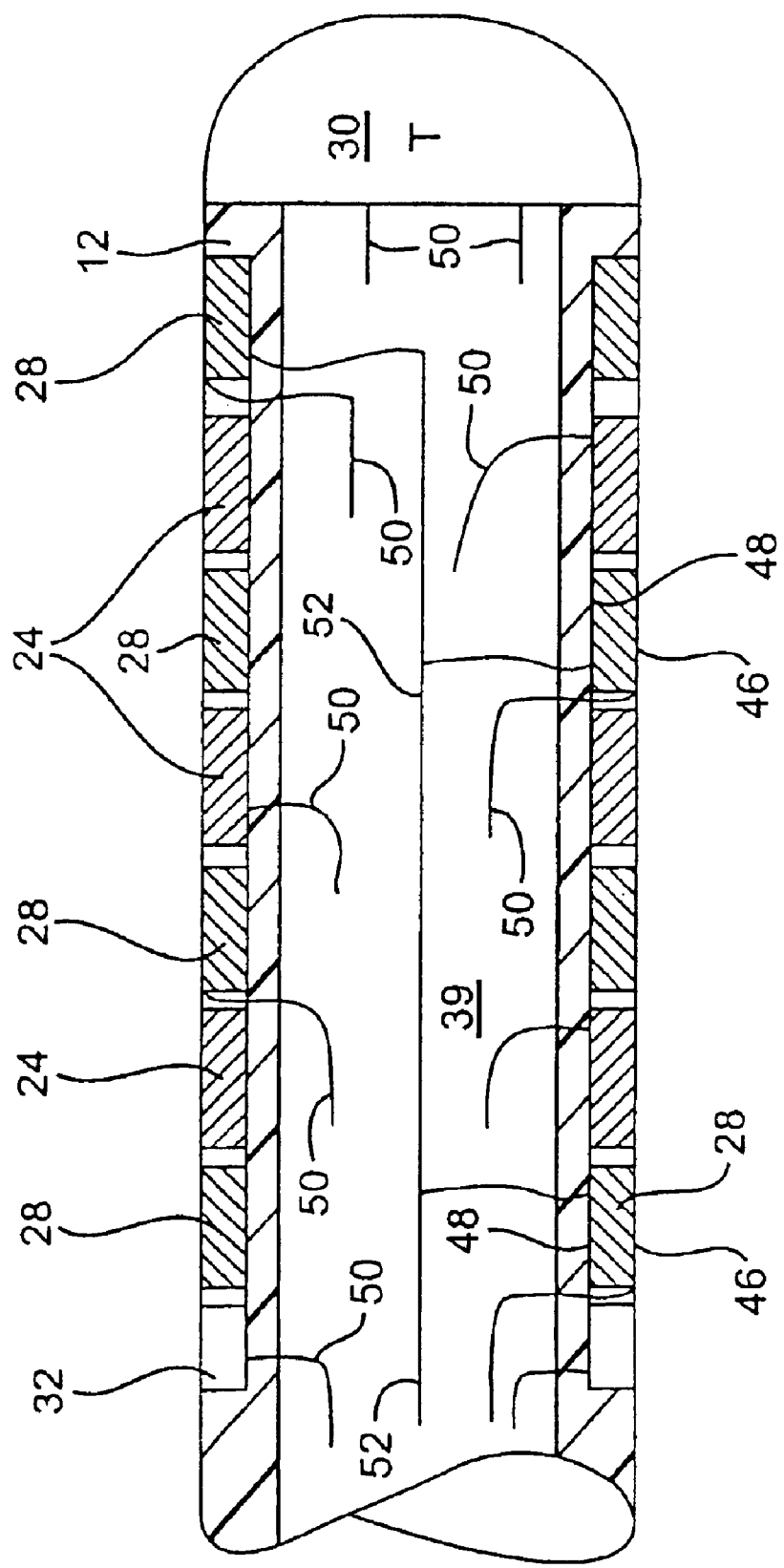
FIGS. 5A and 5B depict alternative embodiments of the tissue ablation apparatus according to the present invention.

FIG. 5A depicts the tissue ablation apparatus shown in FIG. 3 without matching layers 42. As can be seen in FIG. 5A, a plurality of leads 50 are operably attached to thermocouples 30 and 32, to transducer elements 28 and to ablation elements 24. For an embodiment having electrodes for ablation elements 24, each electrode has a single lead 50. Thermocouples 30 and 32 each have a pair of leads 50. Transducer elements 28 have one lead 50 in electrical communication with outer face 46. Further, a ground 52 extends from inner face 48 of transducer 28. As shown in FIG. 5A, a common ground can be used for all transducer elements 28 within a particular apparatus 2. The benefit of using a common ground 52 is that fewer leads or wires 50 are passed from distal end 10, through lumen 39 to controller 23.

Figure 5B:
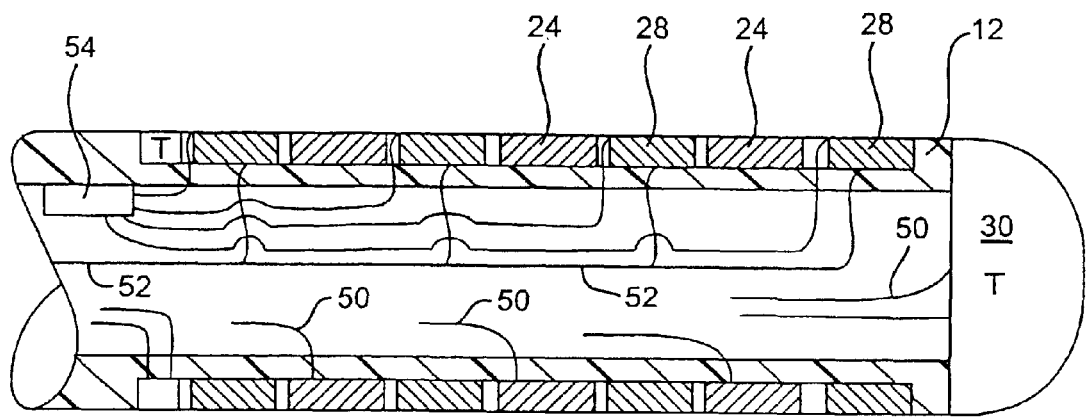

The embodiment shown in FIG. 5B depicts the use of a multiplexer 54 operably attached to distal end 10 of flexible elongate body 12. Multiplexer 54 preferably is operably attached proximal of ablation elements 24 and transducer elements 28. Multiplexer 54 permits the attachment of leads 50 from transducer elements 28 to multiplexer 54 without the need to run those leads 50 to controller 23. Such a configuration can reduce the number of wires needed to be extended through lumen 39 to controller 23.

Figure 6:
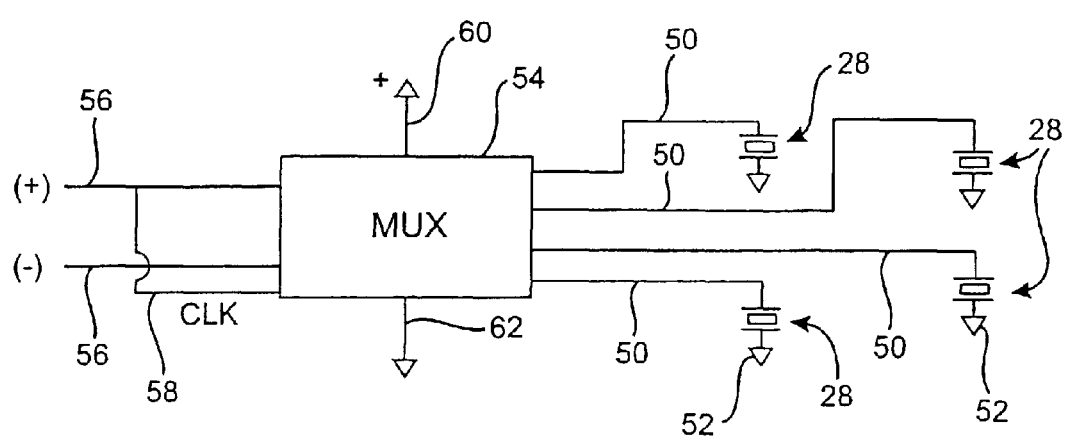
FIG. 6 depicts a schematic of a multiplexer as part of a tissue ablation apparatus.

The operation of multiplexer 54 is best described in conjunction with FIG. 6. FIG. 6 depicts transducer elements 28 each having ground 52 and lead 50. Leads 50 are operably attached to multiplexer 54, preferably on the distal side of multiplexer 54. Multiplexer 54 has a ground 62 and a transmission line 60 for providing power to multiplexer circuit 54. Transmit and receive lines 56 provide a means to transmit electrical signals to multiplexer 54. Multiplexer 54 then directs electrical signals to the appropriate transducer 28. Transmit/receive wires 56 carry transducer 28 excitation signals as differential pulses in series format from controller 23 to multiplexer 54. At multiplexer 54, each excitation signal is routed to an appropriate one of the transducer elements 28 in order to execute an excitation sequence used by controller 23. Similarly, return echoes received by transducer element(s) 28 are transferred to multiplexer 54 and return to controller 23 along transmit/receive lines 56.

By minimizing the number of wires required to carry the excitation signals from controller 23 to each of transducer elements 28, the diameter of elongate body 12, and more specifically, the size of lumen 39 can be reduced. Alternatively, the number of transducer elements 28 can be increased at distal end 10 without the need to require wires to be run through lumen 39 to controller 23.

Multiplexer 54 further may include a clock line 58 extending from controller 23 to multiplexer 54. Such a clock line 58 assists multiplexer 54 in determining which transducer element 28 is to receive an excitation signal. Alternatively, as shown in FIG. 6, clock line 58 operates by counting the number of excitation signals transmitted through transmit/receive lines 56 and incrementing a counter in multiplexer 54 to coordinate the transfer of excitation signals to the appropriate transducer 28. In one embodiment, multiplexer 54 also includes a data line (not shown in FIG. 6) extending from controller 23 to multiplexer 54. This data line permits controller 23 to control the operation of multiplexer 54.

Figure 7A:
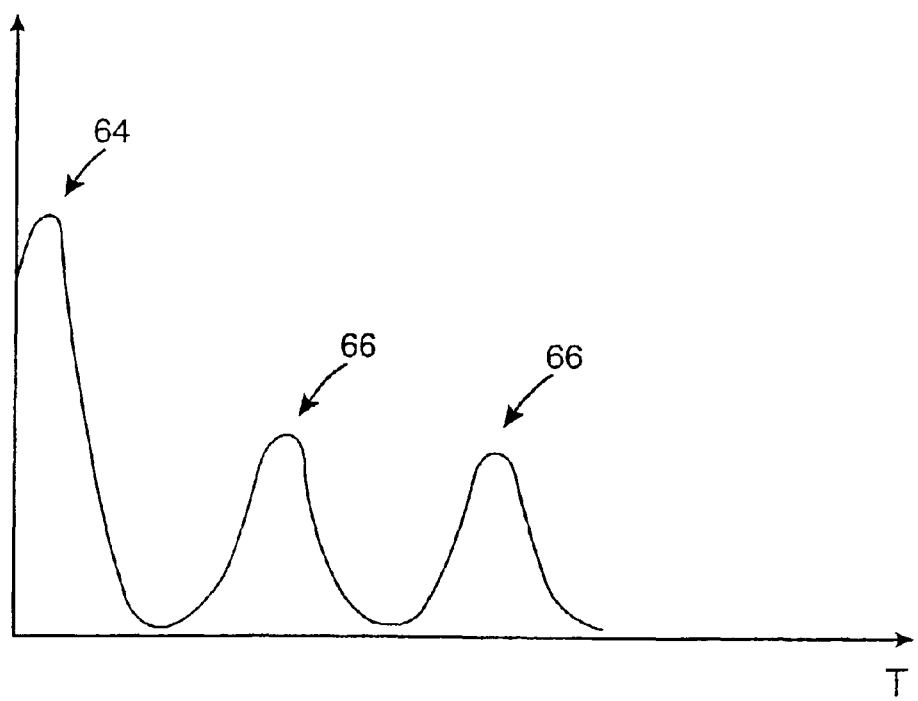
FIGS. 7A–7B depict energizing and reflected signals sent to and received by a transducer element of the present invention.
Figure 7B:
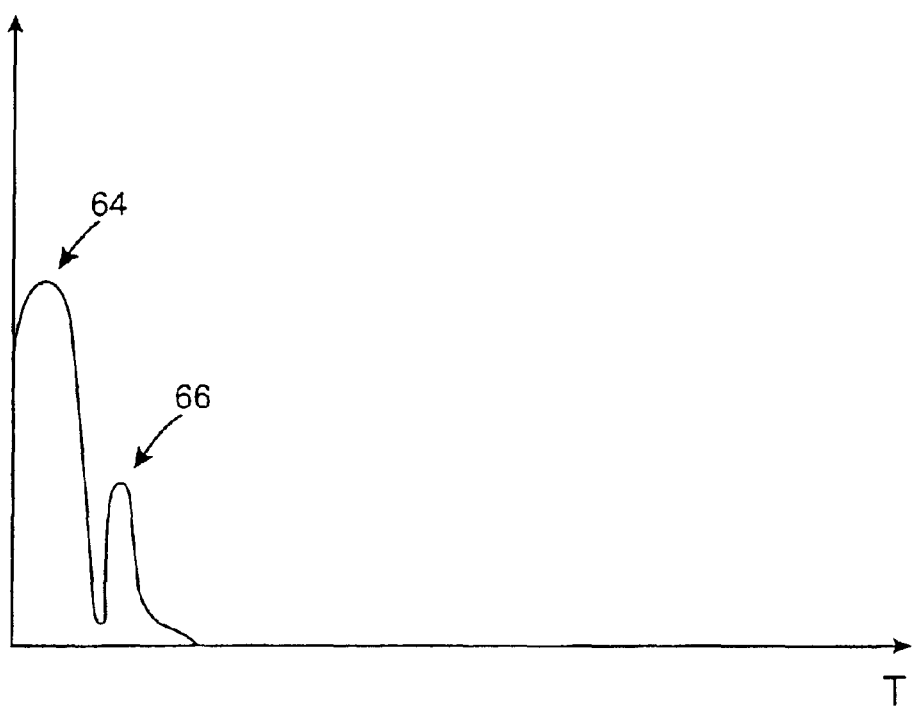
Figure 8:
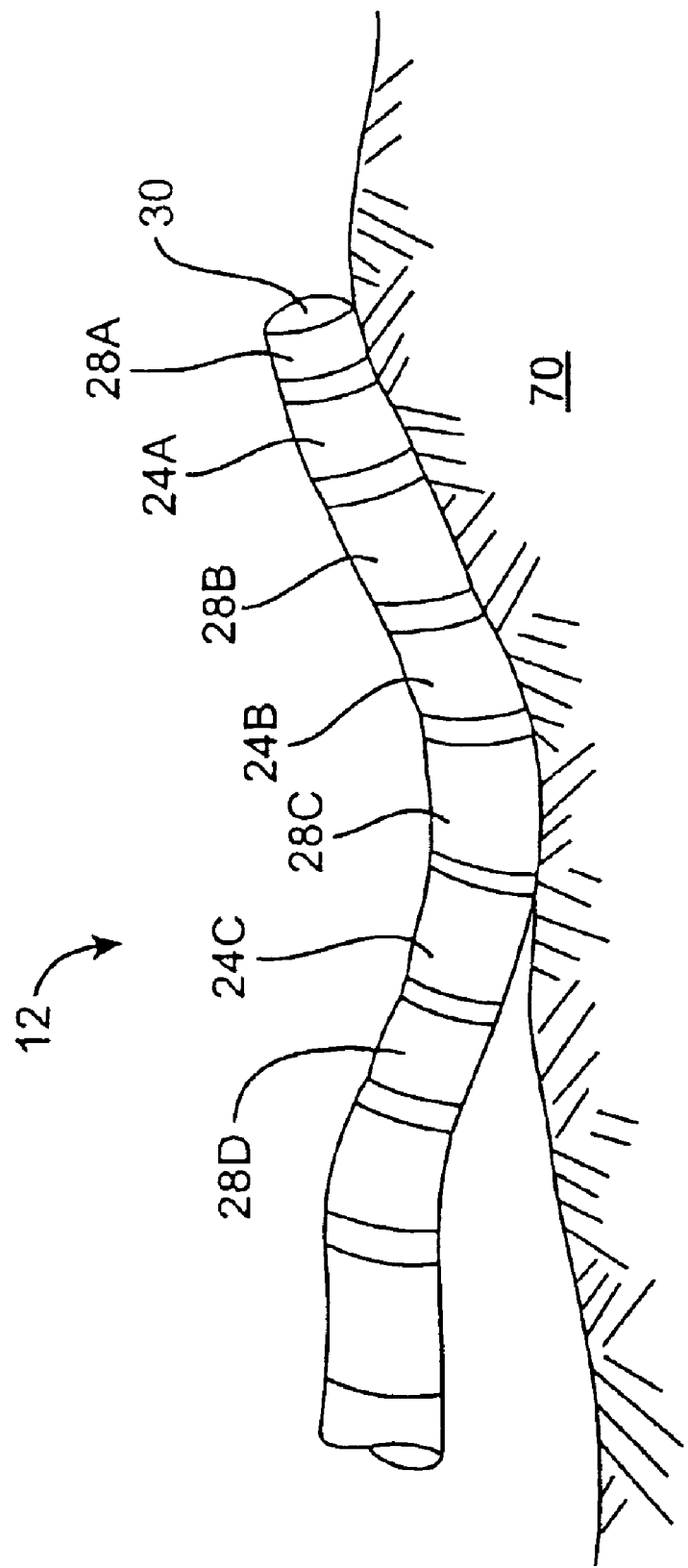
FIG. 8 depicts the tissue ablation apparatus of the present invention in contact with tissue.

Turning now to FIGS. 7 and 8, the operation of tissue ablation apparatus 2 and system 4 will be described. Tissue ablation apparatus 2 operates by having transducer elements 28 detect the proximity of a tissue 70 with respect to elongate body 12 distal end 10. Controller 23 calculates the time delay between transducer element 28 excitation and the receipt of a reflected signal 66 from surrounding tissue 70 to determine the distance between transducer element 28 and tissue 70, as further described below.

As shown by FIGS. 7A and 7B, an excitation signal 64 is transmitted from controller 23 to transducer elements 28, or to multiplexer 54 for transmission to transducer elements 28. Excitation signal 64 is converted by transducer 28 into an ultrasound signal which propagates out into surrounding fluid and tissues within the patient. Transducer elements 28 detect reflected signals 66 and transfer electrical representations of those signals to controller 23 for processing.

Controller 23 uses the time delay between the excitation 64 and the receipt of reflected signal 66 to calculate the approximate distance to the reflecting object. Controller 23 is capable of differentiating between low amplitude blood reflections and larger amplitude tissue reflections 66 as shown in FIG. 7. Controller 23 further differentiates from a randomized back scatter versus more stable tissue scatter. The distance from each transducer 28 to tissue 70 may be calculated by knowing the speed of sound and measuring the time response to the larger amplitude tissue reflections. If the signal completely consists of larger amplitude wave forms, intimate contact will be diagnosed. While transducers 28 inherently have a blind zone/time period in which signals cannot be measured, the resulting blind zone is rather small. For example, for a 30 Mhz transducer, this distance is approximately 0.15 mm. Hence, reflected signal 66 measured almost immediately after excitation 64 occurs results in the distance from the transducer 28 to tissue 70 being less than about 0.15 mm blind distance.

Tissue ablation system 4, therefore, can be operated by inserting tissue ablation apparatus 2 within the patient and positioning distal end 10 of ablation apparatus 2 near a desired location of the patient's anatomy. Transducer elements 28 are energized with excitation signal 64 and reflected signals 66 are received and processed by controller 23. Controller 23 determines whether or not transducer elements 28 are in contact with tissue 70. If at least one transducer element 28 is in contact with tissue 70, ablation using an adjacent ablation element 24 may occur. Preferably, as shown in FIG. 8, it will be desirable to have more than one transducer element 28 in contact with tissue 70.

Controller 23 can be operated in a variety of ways to determine the number and positioning of transducer elements 28 which may be in contact with tissue 70. For example, as shown in FIG. 8, transducer elements 28A, 28B and 28C would indicate that they were in contact with tissue 70. This may permit the physician to ablate tissue 70 using electrode 24A and electrode 24B. Transducer element 28D would not indicate contact with tissue 70. Therefore, it is inconclusive whether ablation element 24C is in contact with tissue 70. Hence, the physician may choose not to ablate with ablation element 24C.

In one embodiment, controller 23 may use a green and red light system for indicating when transducer elements 28 are in contact with tissue 70. In one particular embodiment, for example, controller 23 has a red light and a green light for each transducer element 28A–28D depicted in FIG. 8. The green light would be illuminated by controller 23 when the corresponding transducer element 28 is in contact with tissue 70. Red lights would be illuminated for those transducer elements 28 not in tissue contact.

Alternatively, a single green and red light may be used for apparatus 2, whereby the green light is illuminated by controller 23 only when all transducer elements 28 are in tissue contact. Still another embodiment involves several transducer elements 28 corresponding to a single green/red light set. For example, elements 28A and 28B may have one green light which controller 23 illuminates when both elements 28A and 28B are in tissue contact. The red light corresponding to elements 28A and 28B would be illuminated if one or both transducer elements 28A and 28B are not in contact with tissue 70. It will be appreciated by those skilled in the art that there exist numerous ways within the scope of the present invention for controller 23 to indicate when tissue 70 contact has been achieved by transducer elements 28, including audible tones and the like.

Ablation elements 24 are preferably used for monopolar ablation, although bi-polar ablation also is anticipated within the scope of the present invention. Ablation elements 24 preferably comprise electrodes. In this manner, RF ablation may occur using ablation elements 24.

Alternatively, ablation elements 24 may comprise ablation ultrasound transducers. In this manner, transducer elements 28 are operated in pulse mode to determine their distance from tissue 70. Upon tissue contact, ablation transducers 24 would be used to ablate tissue 70. The use of transducers for acoustic ablation is further described in U.S. Pat. No. 5,630,837, the complete disclosure of which has been previously incorporated by reference.

Alternatively, transducer elements 28 can be used to both image and ablate tissue 70. Transducer elements 28 would first be operated in pulse mode, to determine whether transducer elements 28 are in contact with tissue 70. Transducer elements 28 then would receive a continuous wave or gated continuous wave electrical signal having a frequency of about 10–15 MHz, and transducer elements 28 would ablate tissue 70 using ultrasound ablation.

The invention has now been described in detail. However, it will be appreciated that certain changes and modifications may be made. For example, while FIGS. 2, 3, 5 and 8 depict transducer elements 28 interspaced between all ablation elements 24, transducers 28 may only exist between some of ablation elements 24 and in some gaps 26. Therefore, the scope and content of this invention are not limited by the foregoing description. Rather, the scope and content are to be defined by the following claims.

What is claimed is:

1. A method of precisely positioning a catheter with respect to a tissue, the method comprising:

providing a catheter system comprising:
- a flexible elongate body having a proximal end and a distal end;
- a plurality of spaced apart electrodes operably attached to the flexible body near the distal end;
- a plurality of transducer elements disposed between at least some of the electrodes; and
- a controller electrically coupled to the plurality of electrodes and the plurality of transducer elements;

inserting the flexible elongate body into a patient;

positioning the elongate body to be proximate a tissue using the plurality of transducer elements; and activating at least one of the electrodes to ablate the tissue if the controller determines that at least two of the transducer elements are in contact with the tissue, the at least one electrode being disposed between the two transducer elements.

2. The method as in claim 1 wherein at least one of the plurality of electrodes comprises an ablation electrode and has at least one of the plurality of transducer elements adjacent thereto, the adjacent transducer element for use in determining whether the ablation electrode is in contact with the tissue to be ablated.

3. The method as in claim 2 wherein the ablation electrode comprises a tip electrode.

4. The method as in claim 1 wherein the plurality of electrodes comprise ring electrodes.

5. The method as in claim 1 wherein the plurality of transducer elements comprise ultrasound transducer elements.

6. The method as in claim 1 wherein the plurality of electrodes are electrically isolated from the plurality of transducer elements.

7. The method as in claim 6 wherein the catheter system further comprises a plurality of spaced apart insulators operably coupled to the flexible body so as to electrically isolate the plurality of electrodes and the plurality of transducer elements.

8. The method as in claim 1 wherein positioning the elongate body comprises determining a distance to the tissue using at least some of the transducer elements.

9. The method as in claim 1 wherein the controller comprises a tissue imaging controller.

10. The method as in claim 1 wherein the controller comprises a tissue ablation controller.

11. The method as in claim 1 wherein each electrode has at least one transducer element adjacent thereto.

* * * * *